United States Patent [19]

Woltersdorf et al.

[11] 4,277,602
[45] Jul. 7, 1981

[54] 3-AMINO-5-SUBSTITUTED-6-HALO-N-(3,4-DIHYDRO-6-SUBSTITUTED-1,3,5-TRUAZIN-2-YL)2-PYRAZINECARBOXAMIDES

[75] Inventors: Otto W. Woltersdorf, Chalfont; Edward J. Cragoe, Jr., Lansdale, both of Pa.

[73] Assignee: Merck & Co., Inc., Rahway, N.J.

[21] Appl. No.: 165,312

[22] Filed: Jul. 2, 1980

[51] Int. Cl.$^3$ .............................................. C07D 251/10
[52] U.S. Cl. .................................... 544/207; 544/212; 424/249
[58] Field of Search .............................. 544/212, 207

[56] References Cited

U.S. PATENT DOCUMENTS 4,085,211  4/1978  Cragoe et al. .................... 424/250

Primary Examiner—John M. Ford
Attorney, Agent, or Firm—Raymond M. Speer; Michael C. Sudol, Jr.

[57] ABSTRACT

This invention relates to 3-amino-5-substituted-6-halo-N-(3,4-dihydro-6-substituted-1,3,5-triazin-2-yl)-2-pyrazinecarboxamides and processes for preparing same. The compounds are eukalemic/saluretic agents useful in the treatment of edema and hypertension.

4 Claims, No Drawings

3-AMINO-5-SUBSTITUTED-6-HALO-N-(3,4-DIHYDRO-6-SUBSTITUTED-1,3,5-TRUAZIN-2-YL)2-PYRAZINECARBOXAMIDES

BACKGROUND OF THE INVENTION

The background to this invention, U.S. Pat. No. 3,313,813 patented Apr. 11, 1967 and issued to Edward J. Craoge, Jr., shows novel (3-amino-5,6-disubstituted-pyrazinoyl)guanidine compounds. The compounds of the U.S. Pat. No.3,313,813 patent are useful because they possess diuretic and natriuretic properties. They differ from most of the known, effective diuretic agents, however, in that the compounds of the U.S. Pat. No.3,313,813 patent selectively enhance the excretion of sodium ions while simultaneously causing a decrease in excretion of potassium ions. The potassium loss, which is caused by known diuretics, often results in a severe muscular weakness. Since the compounds of the U.S. Pat. No. 3,313,813 patent prevent the potassium depletion, they have this decided advantage as diuretics. As diuretic agents, they can be used for the treatment of edema, hypertension and other diseases or conditions known to be responsive to this therapy and are especially useful when used in combination with or concomitantly with potassium losing diuretic agents.

It has been found in U.S. Pat. No. 3,313,813 that the pyrazinoylguanidine compounds therein described when co-administered with other diuretic agents known to enhance the elimination of potassium ions along with sodium ions, will maintain the potassium ion excretion at approximately the normal or control rate and thus overcome this undesirable property of other diuretic agents.

In actuality, applicants' compounds in the instant case as further described, accomplish the objective previously achieved by using a combination of pyrazinoyl-guanidine compounds of the U.S. Pat. No. 3,313,813 patent with diuretic agents which cause elimination of sodium with concomitant excessive potassium elimination. Thus, the compounds of the instant case are effective eukalemic/saluretic agents. Since the compounds of the instant invention are thus eukalemic/saluretic agents, they constitute single entities which are useful for the treatment of edema and hypertension and other diseases or conditions known to be responsive to this therapy.

SUMMARY OF THE INVENTION

The instant case covers novel 3-amino-5-substituted-6-halo-N-(3,4-dihydro-6-substituted-1,3,5-triazin-2-yl)-2-pyrazinecarboxamides and a process for preparing the same. The novel compounds of this invention are depicted in Formula I

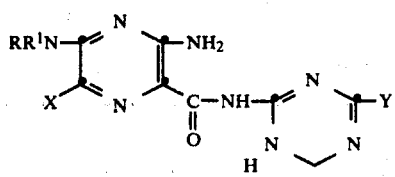

wherein
R and $R^1$ are the same or different and are hydrogen or $C_{1-5}$ alkyl, $C_{2-5}$ alkenyl or $C_{3-6}$ cycloalkyl;
X is halo such as chloro, bromo, iodo or fluoro;
Y Is OH or $NHR^2$ wherein $R^2$ $C_{1-5}$ lower alkyl and the pharmaceutically acceptable acid addition salts thereof.

In the above formula, $C_{1-5}$ alkyl means branched or straight chained alkyl groups such as methyl, ethyl, propyl, n-propyl, butyl, pentyl, isopentyl and the like. $C_{1-5}$ alkenyl is represented by allyl, propenyl and the like and $C_{3-6}$ cycloalkyl is represented by cyclopropyl, cyclohexyl, cyclopentyl and the like.

The invention includes compounds which are the tautomeric forms of the compound of Formula I, namely to tautomeric forms of the formula:

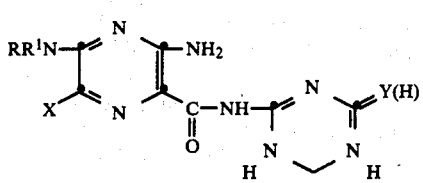

wherein R, $R^1$, $R^2$ and X are as defined for Formula I, and Y is as defined above minus a hydrogen atom.

The preferred compounds of this invention are those compounds of Formula I and the tautomeric forms (Formula II) wherein
R and $R^1$ are hydrogen or $C_{1-5}$ alkyl;
X is chlorine;
Y is —OH,
and the pharmaceutically, acceptable salts thereof.

The compounds of this invention as shown by Formula I and the preferred compounds discussed above are useful because they possess diuretic and natriuretic properties. In addition, they are useful eukalemic saluretics, in other words, the compounds of the instant case cause neither loss or abnormal retention of potassium ions. In contradistinction, the pyrazinoylguanidine compounds of U.S. Pat. No. 3,313,813 do cause a decrease in the excretion of potassium ions. However, other well known diuretics such as furosemide, chlorothalidone and acetazolamide cause an increase in potassium excretion which often results in muscular weakness. Applicants' compounds combine in a single agent the advantages of a combination of the known pyrazinoylguanidine diuretics of U.S. Pat. No. 3,313,813 which decrease potassium with the known diuretics which cause a potassium loss. Thus, the compounds of this invention maintain the excretion of potassium at approximately normal levels while causing an increased renal elimination of sodium ions and water which is the desirable characteristic of the diuretic.

Also covered within the scope of the above Formula I compounds and the preferred compounds are the pharmaceutically acceptable acid addition salts thereof. These salts can be made by reacting the free base with a pharmaceutically acceptable acid such as for example, hyrochloric acid, sulfuric acid, hydrobromic acid or isethionic acid. These salts, as stated above, are to be considered as included in this invention.

The products of this invention can be administered to patients (both human and animal) in the form of pills, tablets, capsules, elixirs, injectable preparations and the like. They can be administered either orally or parentally or any other feasible method as known to those skilled in the art such as intravenously or in the form of suppositories and the like.

The type of formulation to be administered can be comprised of one or more of the compounds of this invention as the only essential active ingredient of the pharmaceutical formulation. The formulation are merely combinations of the active ingredient mentioned with pharmaceutically inert carriers and the like.

The compounds of this invention are advantageously administered at a dosage range of from about 5 mg. to about one gram per day or a somewhat higher or lower dosage at the physician's discretion, preferably in subdivided amounts on a 2 to 4 times a day regimen and most preferably at a dosage range from 10 to 500 mg. per day. It will be realized by those skilled in the art that the dosage range for any particular patient (animal or human) will depend upon the severity of the disease treated, weight of the patient and any other condition which the physician or other person skilled in the art will take account of.

The compounds disclosed in this invention in Formula I and the tautomeric forms of Formula II can be formed by the process depicted in the following equation:

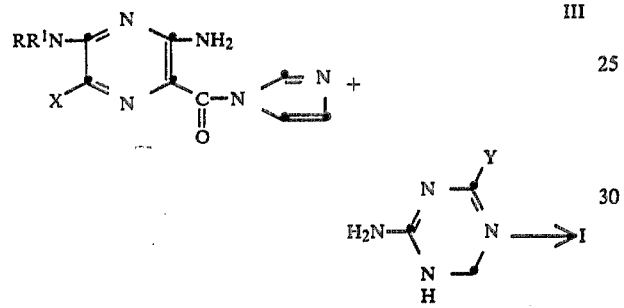

This process involves reacting an active pyrazinoic acid amide such as the imidazole amide III with a 2-amino-3,4-dihydro-1,3,5-triazine to obtain the desired product. The reaction is conducted in a suitable solvent such as dimethylformamide, dimethylsulfoxide and the like at a temperature of from 25° C. to the boiling temperature of the solvent but preferably from 50° C. to 100° C. The reaction is usually conducted with an excess of the triazine component and the desired product is isolated by filtration of the cooled reaction or by treatment of the reaction solution with water followed by filtration of the product.

The following examples are included to illustrate the preparation of compounds of this invention and also to illustrate the preparation of a representative dosage form.

EXAMPLE 1

3,5-Diamino-6-chloro-N-(3,4-dihydro-6-hydroxy-1,3,5-triazin-2-yl)-2-pyrazincecarboxamide To a solution of 3,5-diamino-6-chloropyrazinoic acid (1.89 g., 0.01 mole) in dimethylformamide (80 ml.) is added 1,1'-carbonyldiimidazole (1.62 g., 0.01 mole). The reaction mixture is stirred for 1 hour in a nitrogen atmosphere to form, in situ, 1-(3,5-diamino-6-chloropyrazinoyl)-imidazole, which is treated with 2-amino-3,4-dihydro-6-hydroxy-1,3,5-triazine (2.1 g., 0.02 mole). The reaction mixture is heated at 95° C. for two hours during which time the 3,5-diamino-6-chloro-N-(3,4-dihydro-6-hydroxy-1,3,5-triazin-2yl)-2-pyrazinecarboxamide which melts at 278°–80° C. separates.

Elemental analysis for $C_8H_9ClN_8O_2$: Calcd.: C, 33.75; H, 3.19; N, 39.36; Found: C, 33.74; H, 3.51; N, 39.18.

EXAMPLE 2

3,5-Diamino-6-chloro-N-(3,4-dihydro-6-ethylamino-1,3,5-triazin-2yl)-2-pyrazinecarboxamide hydrate To a solution of 3,5-diamino-6-chloropyrazinoic acid (1.89 g., 0.01 mole) in dimethylformamide (80 ml.) is added 1,1'-carbonyldiimidazole (1.62 g., 0.01 mole). The reaction mixture is stirred for 1½ hours in a nitrogen atmosphere to form, in situ, 1-(3,5-diamino-6-chloropyrazinoyl)imidazole, which is treated with 2-amino-3,4-dihydro-6-ethylamino-1,3,5-triazine hydrochloride (2.14 g., 0.012 mole) in water (5 ml.) and 10N sodium hydroxide (1.1 ml., 0.011 mole). The reaction mixture is stirred for 2 hours at 25° C. and 1 hour at 45° C. during which time the 3,5-diamino-6-chloro-N-(3,4-dihydro-6-ethylamino-1,3,5-triazin-2yl)-2-pyrazincarboxamide hydrate, which melts at 205° C., precipitates.

Elemental analysis for $C_{10}H_{14}ClN_9O.H_2O$; Calcd: C, 36.42; H, 4.89; N, 38.23; Found: C, 36.80; H, 4.98; N, 38.23.

EXAMPLE 3

| Compressed Tablet containing 50 mg. of active ingredient. | |
|---|---|
| | Per Tablet, Mg. |
| 3,5-diamino-6-chloro-N-(3,4-dihydro-6-hydroxy-1,3,5-triazin-2-yl)-2-pyrazine-carboxamide | 50 |
| Calcium phosphate dibasic | 200 |
| Ethyl cellulose (as 5% solution in ethanol) | 5 |
| Unmixed granulation | 255 |
| Add: | |
| Starch, corn | 14 |
| Magnesium stearate | 1 |
| | 270 |

Directions: Mix the active ingredient above and calcium phosphate and reduce to a No. 60 mesh powder. Granulate with Ethocel in alcohol and pass the wet granulation through a No. 10 screen. Dry the granulation at 110° F. for 12–18 hours. Dry grind to a No. 20 mesh. Incorporate the "adds" and compress into tablets each weighing 270 mg.

EXAMPLE 4

| Dry filled capsule containing 50 mg. of active ingredients. | |
|---|---|
| | Per capsule, mg. |
| 3,5-diamino-6-chloro-N-(3,4-dihydro-6-ethylamino-1,3,5-triazin-2-yl)-2-pyrazinecarboxamide hydrate | 50 |
| Lactose | 273 |
| Magnesium stearate | 2 |
| Mixed powders | 325 |

Mix the active ingredient above, lactose, and magnesium stearate and reduce to a No. 60 mesh powder. Encapsulate, filling 325 mg. in each No. 2 capsule.

The above formulations can be employed to prepare compressed tablets or capsules of other novel compounds of this invention hereinbefore described.

What is claimed is:

1. A compound of the formula:

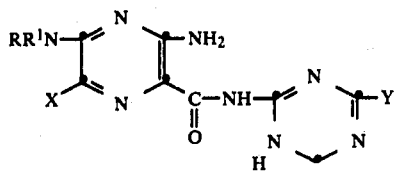

wherein
R is hydrogen, $C_{1-5}$ alkyl, $C_{2-5}$ alkenyl or $C_{3-6}$ cycloalkyl;
$R^1$ is hydrogen, $C_{1-5}$ alkyl, $C_{2-5}$ alkenyl or $C_{3-6}$ cycloalkyl;
X is halo;
Y is hydroxy
the pharmaceutically acceptable acid addition salts thereof and the tautomeric forms thereof 2. A compound of the formula

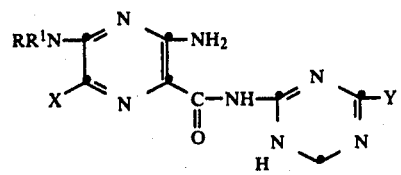

or the tautomeric forms thereof wherein
R is hydrogen or $C_{1-5}$ alkyl;
$R^1$ is hydrogen or $C_{1-5}$ alkyl;
X is chloro;
Y is hdyroxy
and the pharmaceutically acceptable acid addition salts thereof.

3. A compound of claim 2 which is 3,5-diamino-6-chloro-N-(3,4-dihydro-6-hydroxy-1,3,5-triazin-2-yl)-pyrazinecarboxamide hydrate.

4. A process for preparing a compound of the formula:

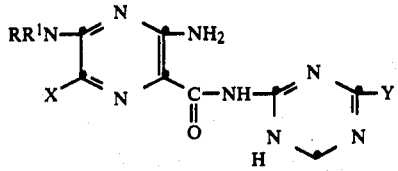

wherein
R is hydrogen, $C_{1-5}$ alkyl, $C_{2-5}$ alkenyl or $C_{3-6}$ cycloalkyl;
$R^1$ is hydrogen, $C_{1-5}$ alkyl, $C_{2-5}$ alkenyl or $C_{3-6}$ cycloalkyl;
X is halo;
Y is hydroxy or $NHR^2$ wherein $R^2$ is $C_{1-5}$ lower alkyl, the pharmaceutically acceptable acid addition salts thereof and the tautomeric forms thereof.
which comprises reacting a compound of the formula:

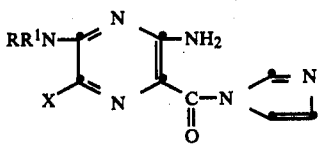

with

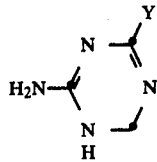

to form the desired product.

* * * * *